United States Patent [19]

Patsch et al.

[11] Patent Number: 5,196,573
[45] Date of Patent: Mar. 23, 1993

[54] PROCESS FOR THE PREPARATION OF SULFONATED ANTHRANILIC ACIDS

[75] Inventors: Manfred Patsch, Wachenheim; Klaus Pandl; Jacques Dupuis, both of Ludwigshafen; Helmut Hagen, Frankenthal, all of Fed. Rep. of Germany

[73] Assignee: BASF Aktiengesellschaft, Ludwigshafen, Fed. Rep. of Germany

[21] Appl. No.: 888,444

[22] Filed: May 28, 1992

Related U.S. Application Data

[63] Continuation of Ser. No. 711,870, Jun. 7, 1991, abandoned.

[30] Foreign Application Priority Data

Jun. 7, 1990 [DE] Fed. Rep. of Germany ....... 4018245

[51] Int. Cl.$^5$ .......................................... C07C 309/29
[52] U.S. Cl. ........................................ 562/57; 562/73
[58] Field of Search .......................................... 562/57

[56] References Cited

FOREIGN PATENT DOCUMENTS 146603 12/1972 Czechoslovakia .
0315046 5/1989 European Pat. Off. .
1380216 10/1964 France .

OTHER PUBLICATIONS

Chemical Abstracts, vol. 88, No. 13, Mar. 27, 1978, p. 486, H. Asakura, et al., "Synthesis of Some Nitrotoluenesulfonic Acids", 88:89276g.
Chemical Abstract, 65171y, vol. 18, 1974, p. 89, M. Kazimierczak, et al., "Preparation of 4-Sulfoanthranilic Acid by the Oxyreduction Method".
Houben-Weyl, Methoden der Organischen Chemie, vol. 11/1, pp. 360-490, "Stickstoff-Verbindungen II" (1957).

Primary Examiner—Nicky Chan
Attorney, Agent, or Firm—Oblon, Spivak, McClelland, Maier & Neustadt

[57] ABSTRACT

A process for the preparation of 4-sulfonated anthranilic acids by sulfonation of ortho-nitrotoluenes with chlorosulfonic acid or oleum followed by oxidation of the methyl group and, finally, reduction of the nitro group.

3 Claims, No Drawings

PROCESS FOR THE PREPARATION OF SULFONATED ANTHRANILIC ACIDS

This application is a continuation of application Ser. No. 07/711,870, filed on Jun. 7, 1991, now abandoned.

The present invention relates to a novel process for the preparation of 4-sulfonated anthranilic acids by sulfonation of ortho-nitrotoluenes with chlorosulfonic acid or oleum followed by oxidation of the methyl group and, finally, reduction of the nitro group.

It is known to convert 4-methyl-3-nitrobenzenesulfonic acid to 4-hydroxy-sulfonylanthranilic acid by treatment with caustic soda solution in the presence of oxides of copper, manganese or iron (Chem Abstr Vol. 81, 65171 g. 1974).

In addition, CS-A 143,603 discloses the preliminary treatment of 4-methyl-3-nitrobenzenesulfonic acid with caustic soda or caustic potash, initially at elevated temperature, accompanied by UV irradiation. The resulting nitrobenzenesulfonic acid is then reduced to the corresponding amino compound with zinc.

However, the cited processes produce the target product in unsatisfactory yields accompanied by numerous by-products It is thus an object of the present invention to provide a novel process for the preparation of sulfonated anthranilic acids which no longer suffers from the above drawbacks. In addition, the starting materials for the novel process are to be the corresponding ortho-nitrotoluenes, since all of the prior art methods make use of a nitrotoluenesulfonic acid as starting material, which must be prepared separately.

We have now found that the preparation of anthranilic acids of formula I

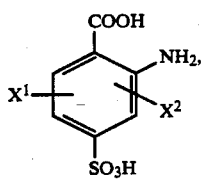
(I)

in which $X^1$ and $X^2$ are the same or different and independently denote hydrogen, halogen or amino. is advantageously carried out by a) treating, in a first stage, a nitrotoluene of formula II

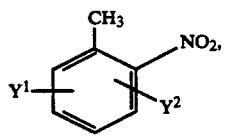
(II)

in which $Y^1$ and $Y^2$ are the same or different and independently denote hydrogen, halogen or nitro, with chlorosulfonic acid or from 10 to 75% w/w oleum at a temperature of from 40° to 150° C. and, b) in a second stage, diluting in situ the resulting reaction mixture containing the nitrotoluenesulfonic acid of formula III

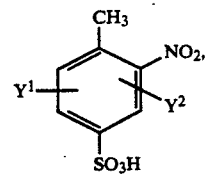
(III)

in which $Y^1$ and $Y^2$ have the meanings stated above, with water and treating the mixture with nitric acid in the presence of a vanadium(V) compound at from 130° to 170° C. and, c) in a third stage, reducing the resulting nitrobenzoic acid of formula IV

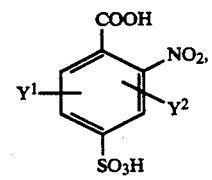
(IV)

in which $Y^1$ and $Y^2$ have the meanings stated above.

The process of the invention is advantageously carried out by placing the nitrotoluene of formula II in a reaction vessel and slowly stirring in the sulfonating agent, i e. chlorosulfonic acid or 10-75% oleum, at a temperature of from 40° to 150° C. Stirring is then continued for from about 0.5 to 5 hours at a temperature of from 40° to 150° C. in the case of chlorosulfonic acid preferably at from 100° to 150° C. and in the case of 10-75% oleum at from 40° to 100° C.

For each mole of nitrotoluene II there will usually be used from 1 to 1.3 moles of sulfonating agent. The treatment of the nitrotoluene II with 10-75% oleum and preferably with 20-30% oleum is preferred.

On completion of the sulfonation, the resulting reaction mixture containing the nitrotoluenesulfonic acid III is diluted with water in situ, i.e. the nitrotoluenesulfonic acid is not isolated.

It is preferred to adopt a procedure in which the amount of water added is sufficient to cause the reaction mixture to contain a 60-85% w/w aqueous sulfuric acid.

To this reaction mixture there is then added the vanadium(V) compound. It is preferred to add vanadium pentoxide, which is converted under the conditions of the reaction to vanadium(V) sulfate.

Nitric acid is then added, the strength of the acid usually being from 30 to 100% w/w. The treatment with nitric acid is carried out at a temperature of from 130° to 170° C. preferably from 145° to 160° C. and more preferably from 150° to 160° C. During such treatment it is possible to distil off dilute nitric acid (approx strength 30% w/w) concurrently from the reaction mixture.

For each mole of nitrotoluene II there will usually be used from 0.01 to 0.1, preferably from 0.03 to 0.06, mole equivalent of vanadium(V) compound and from 1.2 to 6 moles of nitric acid.

On completion of the reaction, which generally takes from 6 to 10 hours, isolation of the nitrobenzoic acid IV is carried out. To this end, the reaction mixture is cooled and water is added thereto in an amount which is usually from 100 to 200% of the weight of the reaction mixture. An aqueous alkali metal hydroxide solution, e.g. caustic soda solution or caustic potash solution is then added until the pH is about 0 to 1.

On cooling to about 0° C. the nitrobenzoic acid IV forms a precipitate, which is separated and then subjected to hydrogenation, normally without further purification.

Alternatively, isolation of the nitrobenzoic acid IV can be dispensed with, in which case it is reduced in situ, as formed after oxidation.

Reduction of the nitrobenzoic acid IV is carried out by conventional methods such as are described in, say, Houben-Weyl, "Methoden der Organischen Chemie", Vol 11/1, pp. 360 et seq.

Preferably, catalytic reduction is carried out using hydrogen, the catalyst being palladium or, in particular, Raney nickel. Palladium is generally used in the form of a supported catalyst, especially with carbon as the support.

The catalytic hydrogenation is generally carried out in aqueous medium at a temperature of from 20° to 60° C. and under a hydrogen pressure of from 1.0 to 6.0 bar. The pH is usually in the range of 4 to 11. When no more hydrogen is absorbed, the catalyst is usually filtered off and the filtrate is acidified (pH from −0.5. to +3.0, preferably 0 to 1). The precipitated anthranilic acid I is then separated off.

Alternatively, isolation may be effected by spray-drying the reduction solution straight after the catalyst has been filtered off, the target product being obtained either as the free acid or in the form of a salt (e g. alkali metal salt), depending on the pH of the solution.

We have found that when Raney nickel is used as catalyst for the catalytic hydrogenation stage, the reaction velocity can be increased by adding an aliphatic mono- or di-carboxylic acid having from 2 to 10 carbon atoms, e.g. acetic acid, propionic acid or adipic acid, to the reaction mixture. For each mole of nitrotoluene II there will generally be used from 5 to 50 g of carboxylic acid.

The process of the invention can be carried out continuously or batchwise. It produces the target products in good yield and in a good state of purity. Another advantage of the novel process is that, as mentioned above, recourse can be directly made to the nitrotoluenes of formula II as starting materials without having to isolate the sulfonic acids produced therefrom.

The sulfonated anthranilic acids I obtained using the process of the invention are valuable intermediates in the preparation of dyes, e.g. copper formazans such as are described in EP-A 315,046.

The invention is illustrated below by the following Examples.

EXAMPLE 1

Preparation of 2-nitro-4-hydroxysulfonylbenzoic acid 548 g (4 moles) of ortho-nitrotoluene were placed in the reaction vessel. 1.350 g of 24% w/w oleum were added dropwise over 2 hours at about 70° C. Stirring was continued for 30 minutes at this temperature, and then 420 ml of water and 40 g of vanadium pentoxide were added to the reaction mixture, which was then kept at 155° C. while 2.550 ml of 65% w/w nitric acid were metered in over a period of 8.5 hours. At the same time, 2.5 liters of approx. 30% w/w nitric acid were distilled from the reaction mixture.

To the reaction solution there were then added 3,205 ml of water and 801 g of 50% w/w caustic soda solution (pH of reaction mixture approx 0). and the mixture was cooled down to 0° C. during the course of 5 hours. The precipitated 2-nitro-4-hydroxysulfonylbenzoic acid was filtered off in vacuo and washed and dried. Yield 76%.

EXAMPLE 2

Preparation of 4-hydroxysulfonylanthranilic acid 494 g of 2-nitro4hydroxysulfonylbenzoic acid were dissolved in 3.5 l of water at a pH of 6.0 and then hydrogenated with hydrogen (pressure 3 bar) at a temperature of 40° C. using 4 g of a palladium catalyst (10% w/w of palladium on carbon). When hydrogen intake ceased, the catalyst was filtered off.

The filtrate was adjusted to pH 0 with hydrochloric acid, and the resulting precipitate was isolated by filtration. There were obtained 410 g of 4-hydroxysulfonylanthranilic acid.

EXAMPLE 3

Preparation of 4-hydroxysulfonylanthranilic acid

Example 2 was repeated except that the filtrate was spray-dried. There were obtained 440 g of 4-hydroxysulfonylanthranilic acid.

EXAMPLE 4

Preparation of 4-hydroxysulfonylanthranilic acid 494 g of 2-nitro4-hydroxysulfonylbenzoic acid were dissolved in 2.5 l of water containing 50 g of propionic acid at a pH of 4.0 and then hydrogenated with hydrogen (pressure 3 bar) at a temperature of 40° C. using 10 g of Raney nickel as catalyst. When hydrogen intake ceased, the catalyst was filtered off.

The filtrate was adjusted to pH 0 with hydrochloric acid, and the resulting precipitate was isolated by filtration. There were obtained 400 g of 4-hydroxysulfonylanthranilic acid.

EXAMPLE 5

Preparation of 4-hydroxysulfonylanthranilic acid

Example 4 was repeated except that the filtrate was spray-dried. There were obtained 440 g of 4-hydroxysulfonylanthranilic acid.

We claim:

1. A process tor the preparation of an anthranilic acid of formula I

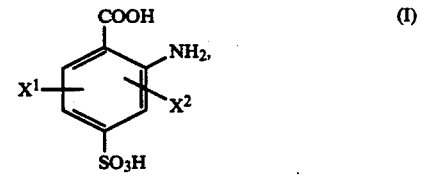

in which
X$^1$ and X$^2$ are the same or different and independently denote hydrogen, halogen or amino, comprising
a) treating in a first stage a nitrotoluene of formula II

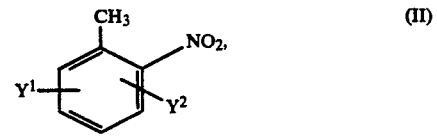

in which $Y^1$ and $Y^2$ are the same or different and independently denote hydrogen, halogen or nitro, with chlorosulfonic acid or from 10 to 75% w/w oleum at a temperature of from 40° to 150° C. and, b) in a second stage, diluting in situ the resulting reaction mixture containing the nitrotoluenesulfonic acid of formula III

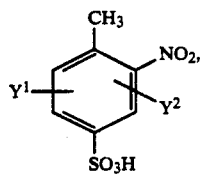

in which $Y^1$ and $Y^2$ have the meanings stated above, with water and treating the mixture with nitric acid in the presence of $V_2O_5$ at from 130° to 170° C. and, c) in a third stage, reducing the resulting nitrobenzoic acid of formula IV

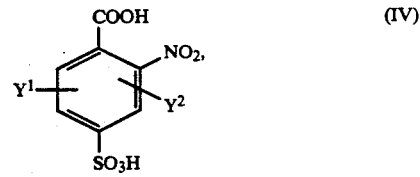

in which $Y^1$ and $Y^2$ have the meanings stated above.

2. A process as claimed in claim 1, wherein $X^1$ and $X^2$ both stand for hydrogen.

3. A process as claimed in claim 1, wherein the treatment of the nitrotoluene of formula II in stage a) is carried out using oleum having a strength of from 10 to 75% w/w.

* * * * *